US012425707B2

(12) United States Patent
Bull et al.

(10) Patent No.: US 12,425,707 B2
(45) Date of Patent: Sep. 23, 2025

(54) ATTACHMENT FOR USE WITH A DEVICE TO SCAN A SURFACE AND A DEVICE FOR THE SAME

(71) Applicant: Imperial College Innovations Ltd, London (GB)

(72) Inventors: Anthony Bull, London (GB); Pierluigi Cuomo, Florence (IT); Marco Hanaman, Florence (IT); Shuqiao Xie, London (GB)

(73) Assignee: Imperial College Innovations Ltd, London (GB)

( * ) Notice: Subject to any disclaimer, the term of this patent is extended or adjusted under 35 U.S.C. 154(b) by 27 days.

(21) Appl. No.: 18/568,519

(22) PCT Filed: Jun. 7, 2022

(86) PCT No.: PCT/GB2022/051423
§ 371 (c)(1),
(2) Date: Dec. 8, 2023

(87) PCT Pub. No.: WO2022/258956
PCT Pub. Date: Dec. 15, 2022

(65) Prior Publication Data
US 2024/0147037 A1 May 2, 2024

(30) Foreign Application Priority Data
Jun. 9, 2021 (GB) ...................... 2108251

(51) Int. Cl.
*H04N 23/51* (2023.01)
*A61B 90/00* (2016.01)
*H04M 1/04* (2006.01)
(52) U.S. Cl.
CPC ........... *H04N 23/51* (2023.01); *A61B 90/361* (2016.02); *H04M 1/04* (2013.01)

(58) Field of Classification Search
CPC ...... A61B 2090/061; A61B 2562/0233; A61B 2562/046; A61B 5/1077; A61B 5/1079;
(Continued)

(56) References Cited

U.S. PATENT DOCUMENTS

| 6,125,338 A | * | 9/2000 | Brienza | G01B 11/24 |
| | | | | 702/167 |
| 2007/0156066 A1 | * | 7/2007 | McGinley | G01B 5/207 |
| | | | | 600/587 |

(Continued)

FOREIGN PATENT DOCUMENTS

| KR | 20150029424 A | 3/2015 |
| WO | 2013109708 A | 7/2013 |
| WO | 2019165227 A1 | 8/2019 |

OTHER PUBLICATIONS

Invitation to Pay Additional Fees for corresponding Application No. PCT/GB2022/051423 dated Sep. 15, 2022, 26 pages.
(Continued)

*Primary Examiner* — Amy R Hsu
(74) *Attorney, Agent, or Firm* — Taft Stettinius & Hollister LLP

(57) ABSTRACT

An attachment for use with a device to scan a surface, for example a bony surface, the attachment comprising: a first housing portion configured to releasably secure a device comprising a camera, a second housing portion connected to the first housing portion and having a wall defining an internal region of the second housing portion and an external region of the second housing portion, and a plurality of pins slidably secured to the wall, each of the plurality of pins having a proximal end disposed in the internal region and a distal end disposed in the external region. Upon abutment of the distal end of each of the pins against a surface, the proximal end of each of the pins is configured to translate relative to the wall. When the device is secured to the first
(Continued)

housing portion, the proximal ends of the plurality of pins are viewable by the camera.

20 Claims, 5 Drawing Sheets

(58) Field of Classification Search
CPC .... A61B 5/4504; A61B 90/361; H04N 23/51; H04M 1/04; G01B 11/24; G01B 5/0004; G01B 5/20
See application file for complete search history.

(56) References Cited

U.S. PATENT DOCUMENTS

| | | | |
|---|---|---|---|
| 2010/0204713 A1* | 8/2010 | Ruiz Morales | B25J 9/041 606/130 |
| 2022/0406452 A1* | 12/2022 | Shelton, IV | A61B 34/37 |
| 2023/0068332 A1* | 3/2023 | Al-Hajri | E21B 47/098 |

OTHER PUBLICATIONS

International Search Report for corresponding Application No. PCT/GB2022/051423 dated Nov. 7, 2022, 14 pages.
Written Opinion for corresponding Application No. PCT/GB2022/051423 dated Nov. 7, 2022, 22 pages.
Search Report for corresponding Application No. GB2108251.6 dated Oct. 15, 2021, 4 pages.

* cited by examiner

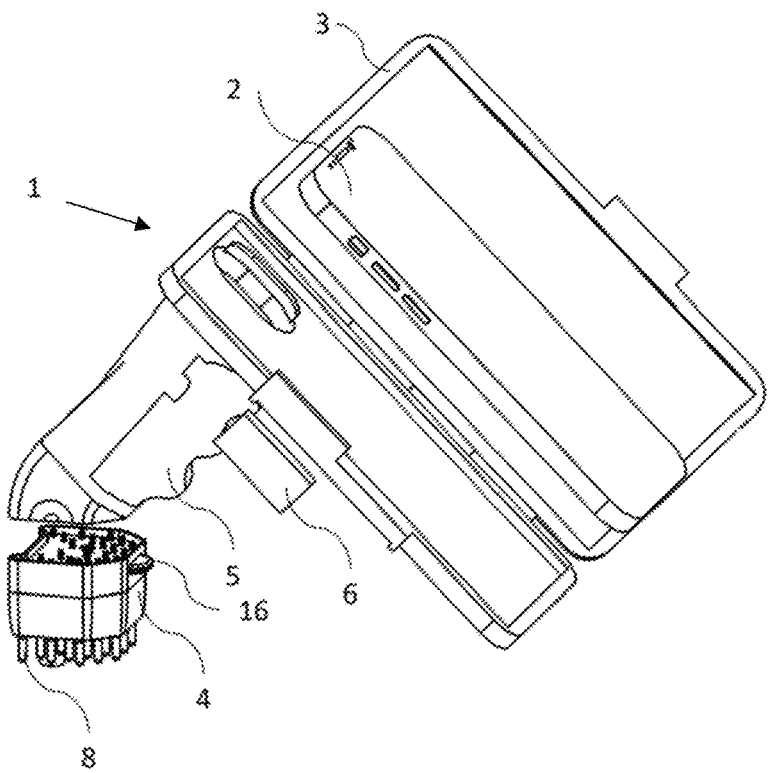
FIG. 1
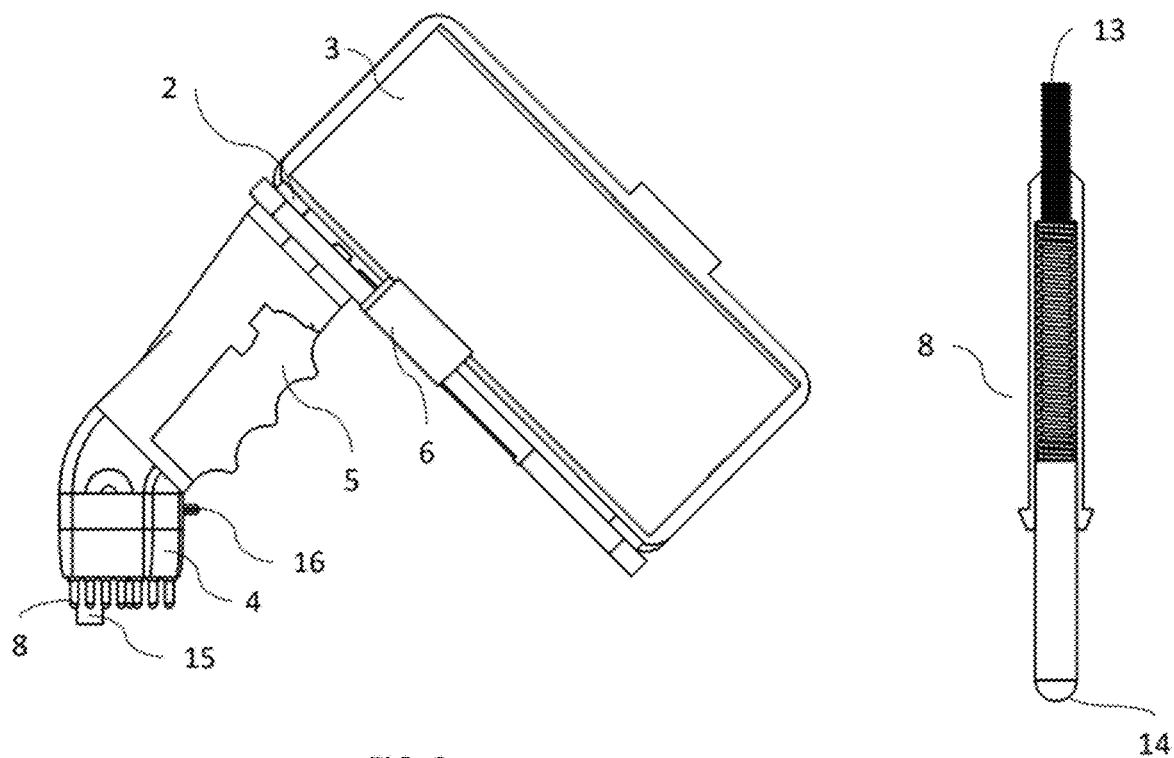
FIG. 2
FIG. 3

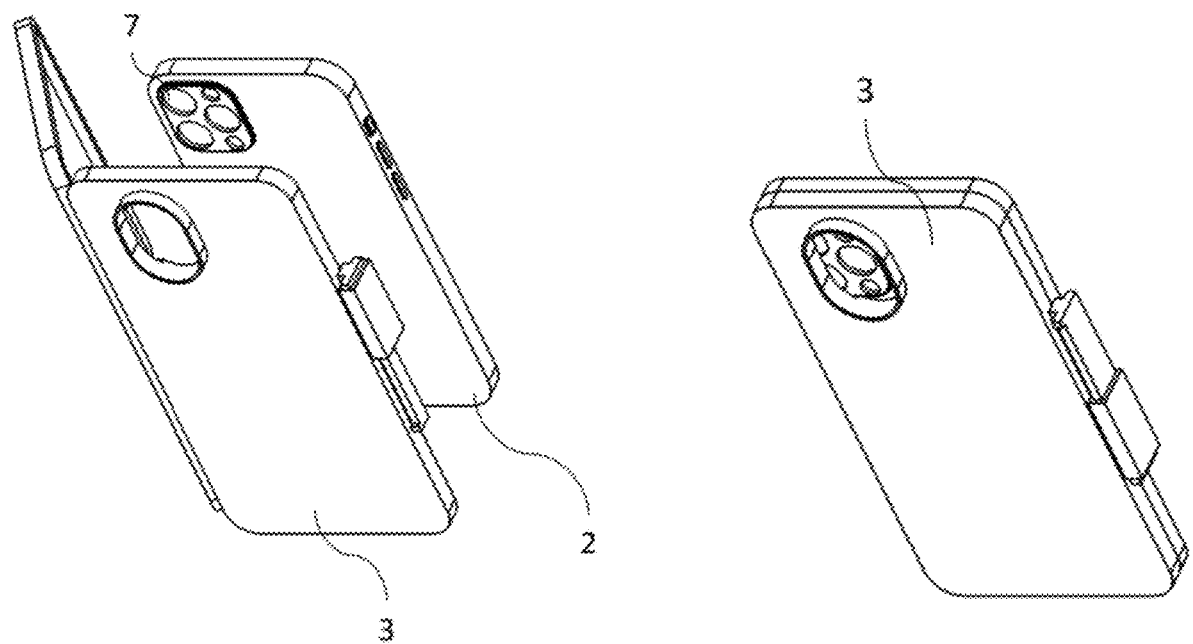
FIG. 4
FIG. 6
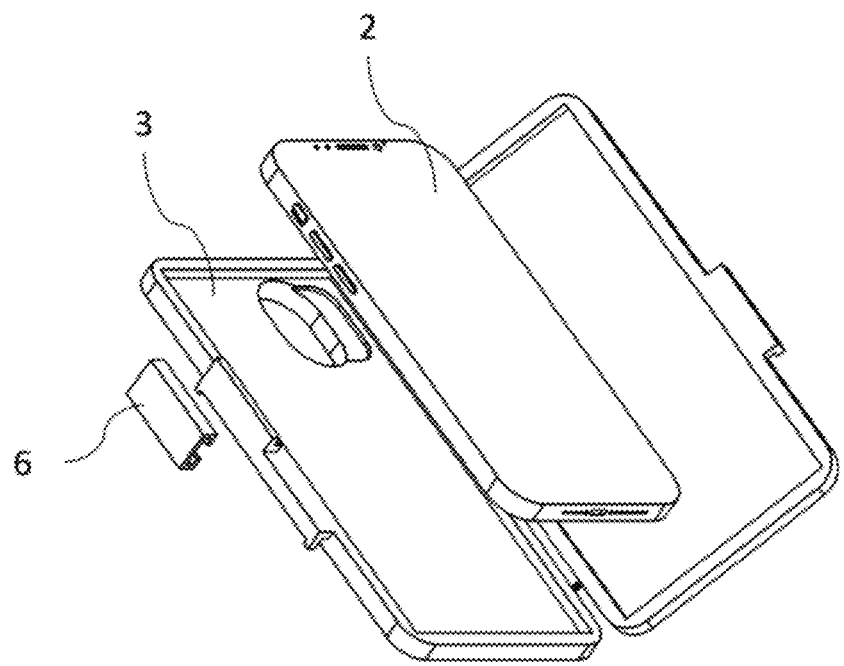
FIG. 5

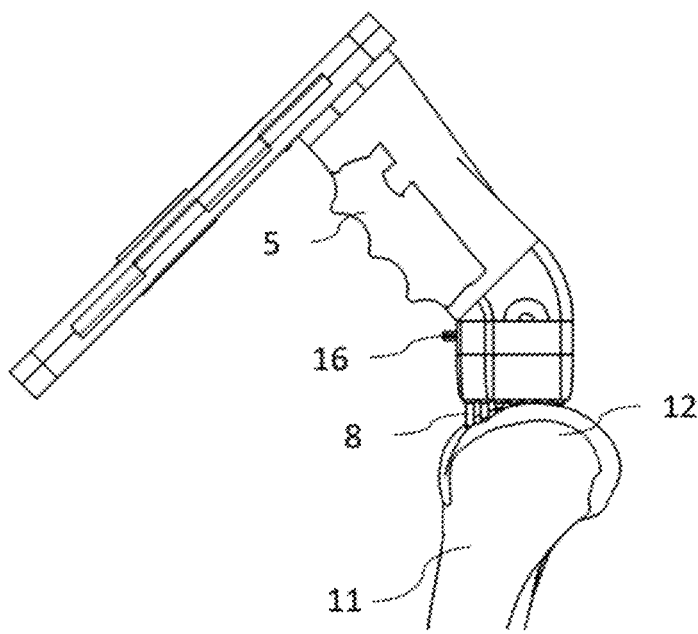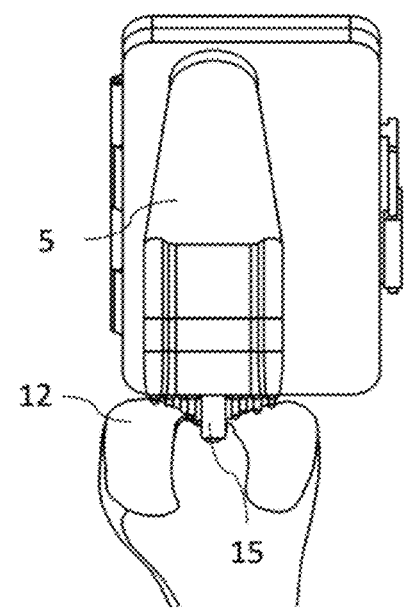
FIG. 7  FIG. 8
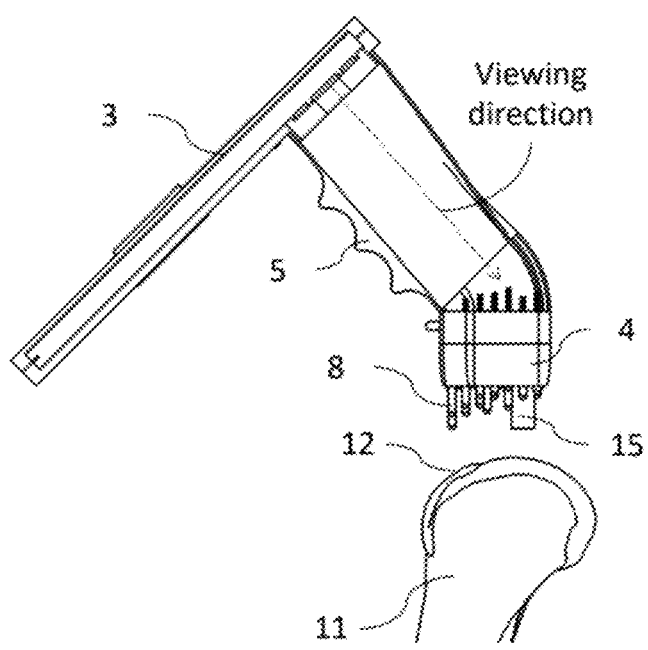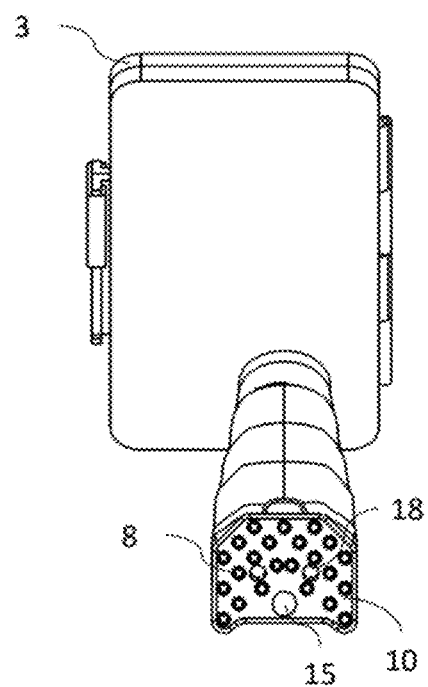
FIG. 9  FIG. 10

ATTACHMENT FOR USE WITH A DEVICE TO SCAN A SURFACE AND A DEVICE FOR THE SAME

CROSS REFERENCE TO RELATED APPLICATIONS

This is a U.S. National Stage Application of, and claims priority to, PCT/GB2022/051423, filed Jun. 7, 2022, which further claims priority to United Kingdom patent application s/n GB 2108251.6, filed Jun. 9, 2021, the contents of each is incorporated herein by reference in its entirety.

This invention relates to an attachment for use with a device to scan a surface and a device for scanning a surface. More specifically, although not exclusively, this invention relates to an attachment for use with a device to scan a bone surface.

BACKGROUND

Orthopaedic implants such as joint replacements require the implant to be fixed in a precise position and orientation in order to function correctly, and to have good longevity. While experience and a pre-clinical plan can help a surgeon correctly perform a bone cut or hole or position the implant, precise positioning is not always possible, particularly where the surgeon does not have any further guidance whilst they are operating and must make a subjective assessment on where to position the implant. This approach can result in implant failure, and as the revision rate for total knee replacement is approximately 7%, in which more than 10% of the implant failure is due to malalignment of the implant, this causes considerable discomfort to the patient. In severe cases this requires revision surgery which results in further cost, inconvenience and discomfort for the patient.

While 3D printed patient-specific instrumentation (PSI), computer navigation and robotic surgery are options for positioning implants during surgery, both of these approaches are prohibitively expensive for the majority of hospitals. Furthermore, PSIs requires considerable experience to produce due to the need to generate a 3D model of the surgical site and the PSI from scan data. Further time and experience is also required to manufacture the PSI and the deliver the device to hospital. Often such scan data is obtained from a CT or MRI scan of the patient which is a further disadvantage of this approach.

BRIEF SUMMARY OF THE DISCLOSURE

Viewed from a first aspect, the present invention provides an attachment for use with a device to scan a surface, for example a bone surface, the attachment comprising: a first housing portion configured to releasably secure a device comprising a camera, a second housing portion connected to the first housing portion and having a wall defining an internal region of the second housing portion and an external region of the second housing portion, and a plurality of pins slidably secured to the wall, each of the plurality of pins having a proximal end disposed in the internal region and a distal end disposed in the external region. Upon abutment of the distal end of each of the pins against a surface, the proximal end of each of the pins is configured to translate relative to the wall. When the device is secured to the first housing portion, the proximal ends of the plurality of pins are viewable by the camera.

Thus, the present invention provides an accurate and cost-effective attachment for use with a device such as a smartphone to scan a surface. A smartphone typically includes one or more cameras, and/or one or more sensors (e.g. accelerometers, gyroscopes, lidar sensors), and/or one or more light sources, and so provides a single integrated device having hardware which enables the surgeon to scan the surface without needing other sensing aspects. The light source from the phone is able to illuminate the pins from within the housing, such that the camera can track the movement of the pins. When used in an operative setting to scan a bone surface, the present attachment enables more accurate and efficient mapping and navigation of a surface in a considerably more cost-effective manner when compared to patient-specific instrumentation and traditional pre-surgical planning. A further advantage is the present attachment can be used as part of existing surgical processes, and thus a surgeon does not need to learn additional techniques, contrary to use of surgical robots. The attachment and mobile phone can function as a positioning system which helps a surgeon find a desired operating point quickly and accurately. Alternatively, when the system is used as a tomography system or a 3D contact scanner, it allows the user to obtain a 3D surface model of the bone without using a CT scanner.

The first housing portion may have a first configuration for securing the device. The first housing portion may have a second configuration for sealing the device within the first housing portion.

The attachment may comprise a post having a distal end. The post may have a variable length and/or a variable diameter. For example, the post may be telescopic, allowing for the surgeon to selectively secure the post at different lengths. The post may be configured to engage the surface so as to position the second housing portion in a known pose relative to the distal end.

The second housing portion may be configured to secure the post in a plurality of different positions. The post may be releasably secured to the second housing portion.

The attachment may comprise a plurality of posts configured to engage the surface. Each post may comprise a respective distal end and each post may define a known pose of the second housing portion relative to the distal end of the respective post.

The second housing portion may be releasably secured to the first housing portion.

The attachment may comprise a locking mechanism operable to selectively lock the pins so as to prevent translation of the pins relative to the side wall. The locking mechanism may comprise a slidable locking plate. In a first position of the locking plate, the plurality of pins can translate relative to the locking plate. In a second position of the locking plate, the locking plate engages plurality of pins to prevent translation of the pins. The locking mechanism may comprise a movable locking member configured to slide the locking plate between the first position and the second position.

One or more of the plurality of pins may comprise a threaded portion. The locking plate may comprise a corresponding threaded portion configured to engage the threaded portion of one or more of the plurality of pins.

The first housing portion may define a viewing direction of the camera. The pins may be arranged substantially parallel to one another. The direction of the pins may define a sensing direction. The second housing portion may be arranged such that the sensing direction is at an angle relative to the viewing direction.

The attachment may comprise a gripping section for a hand of a user. The gripping section may be between the first housing portion and the second housing portion.

A first pin of the plurality of pins may have a different length to a second pin of the plurality of pins. One or more of the plurality of pins may comprise a resiliently deformable element biased to urge the proximal end apart from the distal end of the respective pin. One or more of the pins may be configured as a pogo pin.

The plurality of pins may comprise an anti-reflective surface coating. This advantageously reduces reflections from the pins when viewed by the camera. The surface coating may be applied to the proximal end of the plurality of pins.

The second housing portion may comprise one or more openings for guiding an external component to a predetermined position on the surface. The second housing portion may be configured to connect to a second device for engaging the surface. The second housing portion may be configured as a surgical guide.

The first housing portion may be sterilised. The first housing portion may be configured as a mobile phone case.

There is also provided a device for scanning a surface, for example a bone surface, the device comprising: a first housing portion comprising a camera, a second portion having a wall defining an internal region of the second portion and an external region of the second portion, a plurality of pins slidably secured to the wall, each of the plurality of pins having a proximal end disposed in the internal region and a distal end disposed in the external region. Upon abutment of the distal end of each of the pins against a surface, the proximal end of each of the pins is configured to translate relative to the wall. The device also comprises a post secured to the housing and having a distal end. The post is configured to position the second housing portion in a known pose relative to the distal end. The first housing portion is secured to the second housing portion such that the proximal ends of the plurality of pins are viewable by the camera.

There is also provided a method of scanning a surface, such as a bone surface, the method comprising: providing an attachment as described herein with respect to the first aspect, inserting a device, such as a smartphone, a camera into the first housing portion of the apparatus such that the proximal ends of the plurality of pins in the internal region are viewable by the camera, abutting the apparatus against a surface at a first position on the surface such that one or more of the plurality of pins translates relative to the wall, capturing one or more images of the proximal ends of the pins, and determining a position of the apparatus relative to the said surface.

The step of determining the position of the apparatus relative to the surface may be based on a comparison of the captured images with pre-recorded images of the said surface.

The method may include determining a 3D model of the surface based on the captured images.

The method may comprise determining an indicator to direct a user to a pre-determined position on the surface based on the determined position, and outputting the indicator to the user.

The camera may be any of a video camera, or a depth camera.

The surface may be part of a musculoskeletal joint, such as knee, hip, shoulder or spinal joint. The musculoskeletal joint may be from different species, such as humans or animals.

There is also disclosed a kit of parts comprising an attachment as described herein, and a device configured for use in any of the methods described herein.

BRIEF DESCRIPTION OF THE DRAWINGS

Embodiments of the invention are further described hereinafter with reference to the accompanying drawings, in which:

FIGS. 1 & 2 illustrate an exemplary system before and after assembling;

FIG. 3 illustrates an exemplary pin in the form of a pogo pin;

FIGS. 4 & 5 illustrate a part of attachment with an open first housing portion;

FIG. 6 illustrates a part of the attachment with a closed first housing portion;

FIGS. 7 & 8 illustrate side and back views of an exemplary system for scanning the surface of a distal femur;

FIG. 9 illustrates a cross-sectional side view of an exemplary system for scanning the surface of a distal femur;

FIG. 10 illustrates a rear perspective view of an exemplary arrangement of a plurality of pins;

DETAILED DESCRIPTION

Figure 11:
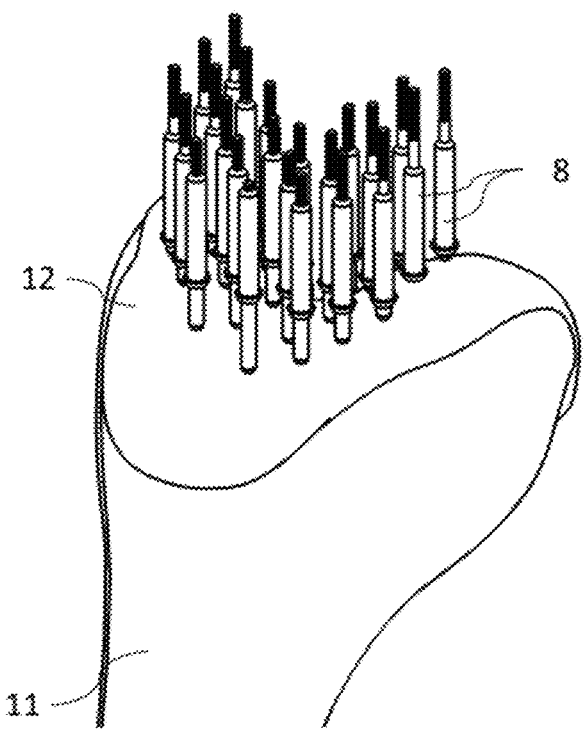
FIGS. 11 & 12 illustrate a plurality of pins pushed against the bony surface with the distal ends of the pins representing the tomography of the bone.

FIGS. 1 & 2 illustrate the system before and after assembling. The system includes an attachment 1 and a mobile phone 2 contained within the attachment 1. The attachment 1 includes a phone case 3, a pin holder 4 and an ergonomic handle 5 between the phone case 3 and the pin holder 4 to aid a user's grip of the system during use. The phone case 3, pin holder 4 and ergonomic handle 5 may be considered as different portions of a housing of the attachment 1. While an ergonomic handle 5 is disclosed, it would be apparent this was not essential to the function of the pin holder 4 or phone case 3 and may be omitted in some cases.

As shown in FIG. 4-6, the phone case 3 is formed of two parts connected by a hinge which allows a user to open the phone case 3 and conveniently insert the mobile phone 2 into the device holder 3. The two parts of the phone case 3 can then be closed to secure the mobile phone 2 within the phone case 3. A slider 6 which engages with corresponding structures on the two parts of the phone case 3 can be used to lock the phone case 2. The camera 7 of the smartphone 2 is shown positioned over a viewing window of the phone case 3. This allows the camera to view an arrangement of pins 8 secured in the pin holder 4 through the viewing window. It is preferable that the camera can view the proximal ends 13 of the pins 8 for scanning the surface as will be explained below. While the viewing window may be formed as a cut out within the phone case 3, it would be apparent this was not essential, and that a section of the phone case may be optically transparent to the camera such that the pins 8 are visible through the phone case 3. When the system is to be used in a sterile environment such as an operating theatre, it is desirable that the phone case 3 hermetically seals the smartphone 2 and the phone case 3 is a sterile component. While a folding phone case is illustrated, it would be apparent this was not essential and phone cases 3 which are not foldable may be used to secure the mobile phone 2. It would be apparent that the attachment 1 could be a single-use disposable item, or may be re-used following a sterilisation process.

While a mobile phone 2, such as a smartphone, is illustrated, this is merely a particularly convenient example of a suitable device that would be used with the present attachment 1. It would be apparent that a mobile phone was not essential, and other devices having a camera and connected to a processor configured to process images obtained from the camera would also be suitable for use with the present attachment. Similarly, while a phone case 3 is described, it would be apparent that any holder that can secure a device in the described manner would be suitable for use in the present attachment.

As shown in FIGS. 7-10, the handle 5 connects the pin holder 4 to the phone case 3. Specifically, the handle 5 connects to the phone case 3 over the viewing window such that the pins 8 are visible to the camera through the handle 5. While the pins 8 are secured in the pin holder 4 in a parallel arrangement to one another and extending substantially perpendicular to the wall 10, it would be apparent that this was not essential. The direction in which the pins 8 translate can be considered as a sensing direction.

The phone case 3 may also be rotatably secured to the handle 5 and/or the pin holder 4 to allow for different viewing angles of the pins 8. For example, the viewing direction of the camera may be at any angle between 30 degrees and 90 degrees relative to the direction of translation of the pins 8 (i.e. the sensing direction). In some cases, the user can adjust the orientation of the pin holder 4 relative to the phone case 3.

As shown in FIGS. 9 & 10, the pin holder 4 includes an arrangement of pins 8 arranged across a wall 10 of the pin holder 4, with the pins 8 having a proximal section located within an internal region of the pin holder 4 and a distal section external to the pin holder 4. The illustrated arrangement of pins 8 is merely exemplary and it would be apparent that other arrangements would be suitable for use in the attachment 1.

Figure 12:
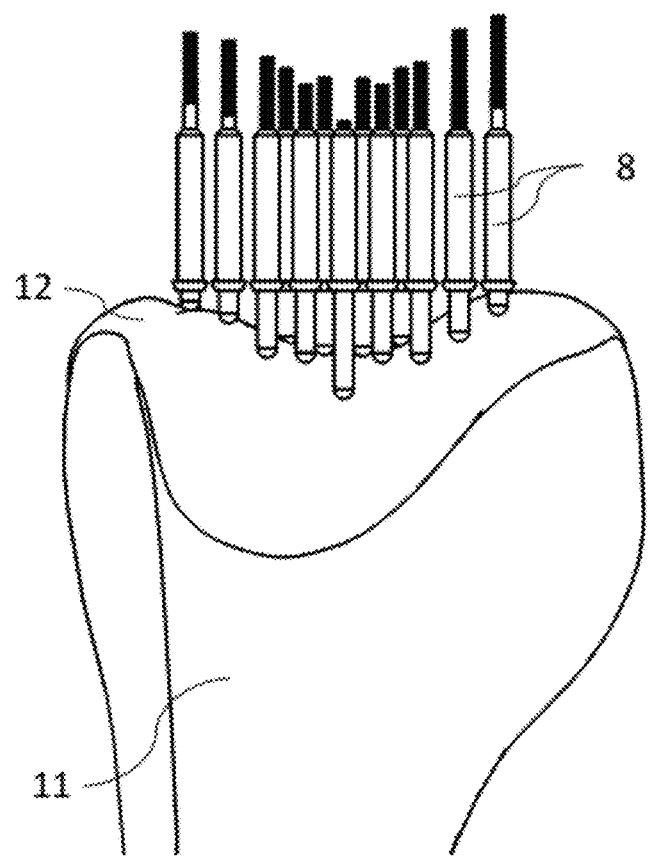

The pins 8 are secured to the wall 10 and extend through the wall 10 from the external region to the internal region. As the pins 8 are slidably secured to the wall 10, pressing the pins 8 against the distal femur 12 causes the pins 8 to translate further into the internal region of the pin holder 4. This translation within the pin holder 4 can then be observed by the camera to determine a corresponding distance at the position of the pin in the external region. The relative displacement between multiple pins 8, such as shown in FIGS. 11 and 12, effectively scans the surface of the distal femur and can be used to derive the tomography of the bone surface 12. As shown in FIG. 3, pogo pins are suitable for use as the pins 8 of the attachment, however it would be apparent this was not essential. The pogo pin has a proximal end 13, a distal end 14 and a spring, or similar resiliently deformable element, biased to urge the distal end 14 away from the proximal end 13. The distal end 14 is also shown having a rounded end for engaging the bony surface 14. While the pins 8 are shown having the same length, it would be apparent that this was not essential, and that pins of different lengths may make up the arrangement of pins used in the present attachment 1.

The pin holder 4 also includes a post 15 which may be shaped and sized for a particular bony surface 12. For example an attachment for use in spinal surgery may utilise a different post 15 compared to an attachment which is to be used in knee or hip or shoulder surgery. It would be apparent that the present attachment is suitable for use in any primary skeletal surgery or orthopaedic surgery. The post 15 functions to position and/or orient the pin holder 4 in a known pose (i.e. position and orientation) relative to a distal end of the post 15. By removing one or more degrees of freedom of the attachment 1, this reduces the effort, and consequently the uncertainty, in correctly positioning the pin holder 4. While an attachment 1 having a single post 15 is shown at the pin holder 4, it would be apparent that two or more posts may be secured to a single attachment 1. The post 15 is also preferably releasably secured to the attachment 1, for example via a threaded connection, to provide greater flexibility of the attachment 1 and its constituent components.

As the post 15 contacts the distal femur 12 at different positions across its surface, the tomography of the surface indicated by the pins 8 will change. The tomography indicated by the pins 8 will also be dependent on the orientation of the pin holder 4 and post 15 when the post 15 contacts the distal femur 12. Thus, by moving the system around the bone (or any other surface) at the same position or at different positions on the bone, a 3D model of the bone (or any other object) can be determined using the smartphone by capturing multiple continuous images of the pins 8.

This scanned tomography can then be compared with other pre-operative scans or 3D models obtained by other modalities, such as CT or MRI imaging, to provide "live" feedback to the user regarding the position and/or orientation of the attachment 1 in relation to the correct position determined in the pre-operative plan. This feedback may be provided in any visual or audible form to guide the surgeon to the correct position and/or orientation. For example, a visual indicator may be displayed on a screen of the mobile phone 2, or transmitted on a remote display. The visual indicator may be overlaid on a live image of the distal femur or onto a 3D model of the distal femur to help the user navigate the distal femur to correctly position the pin holder 4. The pre-operative scans may be loaded onto the smartphone 2, or the images captured by the mobile phone 2 may be transmitted to a local device within the operating room. It is preferable to use an off-line device for processing. By keeping the images on the mobile phone 2, the device does not need to be an on-line device, and therefore there is less risk of electronic interference with other devices in the operating theatre. A further advantage of using a mobile phone 2, is often such devices will include an accelerometer and/or a gyroscope which can provide further sensor inputs when combined with the pin displacements to determine the position and orientation of the pin holder 4 on the bony surface 12. These additional data sources may be used to provide improved intra-operative feedback to guide the user to the correct surgical site. Processing the images obtained via the camera on the mobile phone 2 is particularly advantageous. Furthermore, a mobile phone 2 is also typically able to capture still or moving video images, and thus does not require additional hardware to provide these outputs to the surgeon.

Figure 13:
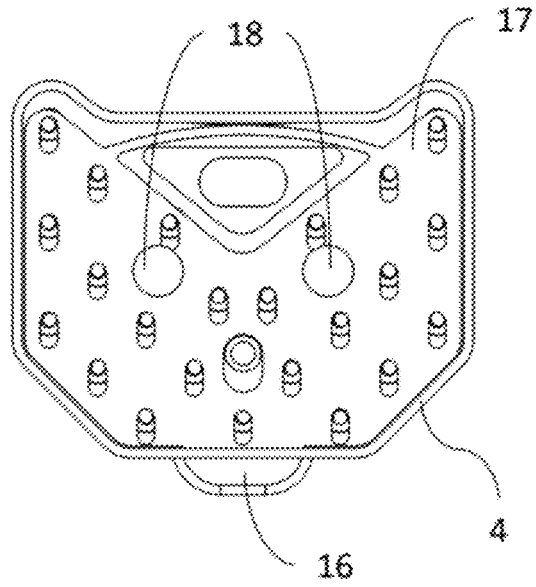
FIGS. 13 & 14 illustrates an exemplary locking mechanism configured to lock the pins in position.
Figure 14:
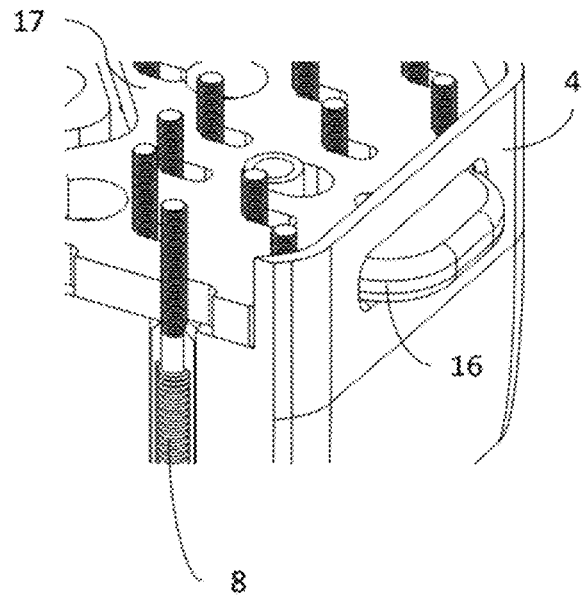
Figure 15:
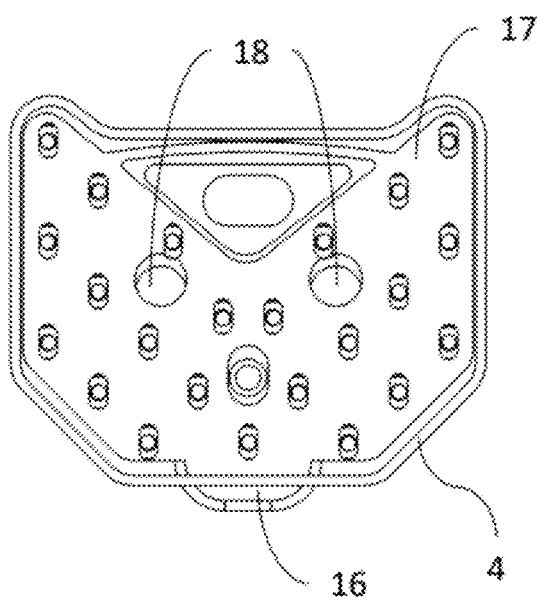
FIGS. 15 & 16 illustrates an exemplary locking mechanism configured to allow the pins to move freely by pushing the locking plates.
Figure 16:
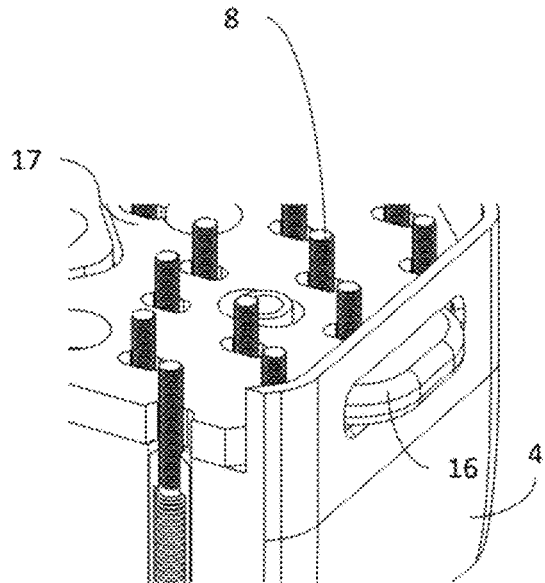

Once the pin holder 4 has been accurately positioned on the bony surface 12, the user is able to lock the pins 8 in position via a locking mechanism connected to the pin holder 4. The illustrated locking mechanism includes a locking key 16 arranged to slide a locking plate 17 into engagement with the pins 8 to lock the pins 8 in position. The pins 8 extend through respective slots formed in the locking plate 17 and when the locking plate 17 is in an unlocked position, as shown in FIGS. 15 & 16, the pins 8 are free to move relative to the locking plate 17. When the locking plate is moved to the locked position, the slots through which the pins 8 extend engage the pins 8 to lock the pins in position as shown in FIGS. 13 & 14. As illustrated, the proximal section of the pins 8 may have a threaded portion which can help to engage a corresponding threaded section of the slots of the locking plate 17. While threaded sections are advantageous, it would be apparent that this was only one example of a suitable engagement between the locking plate 17 and the pins 8 which could lock the pins 8 in position. It would also be apparent that the locking key 18 may slide or rotate to push the locking plate 17 into engagement with the pins 3.

Once the pins 8 are locked in position, holes 18 formed in the wall 10 of the pin holder 4 act as guide holes to guide further components to pre-determined positions on the bony surface 12. The pin holder 4, therefore, effectively becomes a patient-specific surgical guide which can be used to guide surgical devices, such as drill bits, to desired positions on the bony surface 12. However, the present attachment 1 avoids the need and technical skill required to manufacture a customised patient-specific surgical guide, as the pins 8 can be locked in position once the attachment 1 is correctly positioned. A further advantage of the present attachment 1 is the ability to separate the pin holder 4 from the phone case 3 and/or handle 5, as the pin holder 4 is releasably secured to the attachment 1. Once the pins 8 are locked in position, there may be no further need for the mobile phone 2 and/or handle 5 as the pin holder 4 has been guided to the correct position. As such, the surgeon can simply detach the phone case 3 from the handle 5 and/or pin holder 8 to improve access to the surgical site. While a releasably secured pin holder 4 is described, it would be apparent that this was not essential, and the pin holder 4 may remain secured to the attachment 1 for the duration of the procedure. Similarly, the pin holder 4 may be integral with the phone case 3 and/or the handle 5 if present.

While the present concepts have been described in relation to an attachment for a mobile phone 2, it would be apparent that an integrated device including the mobile phone, or a suitable device, may be used instead.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The invention claimed is:

1. An attachment for use with a device to scan a surface the attachment comprising:
    a first housing portion configured to releasably secure a device including a camera,
    a second housing portion connected to the first housing portion and having a wall defining an internal region of the second housing portion and an external region of the second housing portion, and
    a plurality of pins slidably secured to the wall, each of the plurality of pins having a proximal end disposed in the internal region and a distal end disposed in the external region,
    wherein, upon abutment of the distal end of each of the pins against the surface, the proximal end of each of the pins is configured to translate relative to the wall, and
    wherein, when the device is secured to the first housing portion, the proximal ends of the plurality of pins are viewable by the camera.

2. An attachment according to claim 1, wherein the first housing portion has a first configuration for securing the device, and wherein the first housing portion has a second configuration for sealing the device within the first housing portion.

3. An attachment according to claim 1 further comprising a post having a distal end, wherein the post is configured to engage the surface so as to position the second housing portion in a known pose relative to the distal end.

4. An attachment according to claim 3, wherein the second housing portion is configured to selectively secure the post in any one of a plurality of different positions.

5. An attachment according to claim 4, wherein the post is releasably secured to the second housing portion.

6. An attachment according to claim 3, further comprising a plurality of posts configured to engage the surface, wherein each post includes a distal end and defines a known pose of the second housing portion relative to the distal end of the respective post.

7. An attachment according to claim 1, wherein the second housing portion is releasably secured to the first housing portion.

8. An attachment according to claim 1, further comprising a locking mechanism operable to lock the pins so as to prevent translation of the pins relative to the side wall.

9. An attachment according to claim 8, wherein the locking mechanism includes a slidable locking plate, wherein, in a first position of the locking plate, the plurality of pins can translate relative to the locking plate, and wherein, in a second position of the locking plate, the locking plate engages one or more of the plurality of pins to prevent translation of the pins.

10. An attachment according to claim 9, wherein the locking mechanism includes a movable locking member configured to slide the locking plate between the first position and the second position.

11. An attachment according to claim 9, wherein at least one of the plurality of pins includes a threaded portion, and wherein the locking plate includes a corresponding threaded portion configured to engage the threaded portion of the at least one of the plurality of pins.

12. An attachment according to claim 1, wherein the first housing portion defines a viewing direction of the camera, wherein the pins are arranged substantially parallel to one another and define a sensing direction, and wherein the second housing portion is arranged such that the sensing direction is at an angle relative to the viewing direction.

13. An attachment according to claim 1, further comprising a gripping section for a hand of a user, and wherein the gripping section is between the first housing portion and the second housing portion.

14. An attachment according to claim 1, wherein a first pin of the plurality of pins has a different length to a second pin of the plurality of pins.

15. An attachment according to claim 1, wherein one of at least one of the plurality of pins includes a resiliently deformable element biased to urge the proximal end apart from the distal end of the at least one of the plurality of pins.

16. An attachment according to claim 1, wherein at least one of the plurality of pins is configured as a pogo pin.

17. An attachment according to claim 1, wherein at least one of the plurality of pins includes an anti-reflective surface coating.

18. An attachment according to claim 1, wherein the second housing portion includes an openings for guiding an external component to a pre-determined position on the surface.

19. An attachment according to claim 1, wherein the second housing portion is configured to connect to a second device for engaging the surface.

20. A device for scanning a surface the device comprising:
a first housing portion including a camera,
a second portion having a wall defining an internal region of the second portion and an external region of the second portion,
a plurality of pins slidably secured to the wall, each of the plurality of pins having a proximal end disposed in the internal region and a distal end disposed in the external region, wherein, upon abutment of the distal end of each of the pins against a surface, the proximal end of each of the pins is configured to translate relative to the wall, and
a post secured to the housing and having a distal end, wherein the post is configured to position the second housing portion in a known pose relative to the distal end,
wherein the first housing portion is secured to the second housing portion such that the respective proximal ends of the plurality of pins are viewable by the camera.

* * * * *